United States Patent [19]

Crutchfield et al.

[11] 4,150,069
[45] Apr. 17, 1979

[54] PHOSPHATE-CARBOXYLATE COMPOUNDS

[75] Inventors: Marvin M. Crutchfield, Creve Coeur; John N. Rapko, St. Louis, both of Mo.

[73] Assignee: Monsanto Company, St. Louis, Mo.

[21] Appl. No.: 861,477

[22] Filed: Dec. 16, 1977

[51] Int. Cl.$^2$ .............................. C07F 9/14; C07F 9/09
[52] U.S. Cl. ................................................... 260/942
[58] Field of Search ........................................ 260/942

[56] References Cited

U.S. PATENT DOCUMENTS 4,014,959  3/1977  Crutchfield et al. ......... 260/942 OR

OTHER PUBLICATIONS

Pudovik et al, "Chemical Abstracts", Vol. 63, (1965), pp. 13064–13065.

*Primary Examiner*—Anton H. Sutto
*Attorney, Agent, or Firm*—S. M. Tarter; E. P. Grattan; F. D. Shearin

[57] ABSTRACT

Compounds of the following formula:

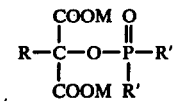

wherein
R is selected from the group consisting of hydrogen and an alkyl group containing from 1 to 4 carbon atoms,
R' is selected from the group consisting of —OB and halogen,
B is alkali metal, ammonium or trialkanolammonium, and
M is selected from B or alkyl having up to 20 carbon atoms, are provided. The salts are useful as detergent builders, and the esters are useful intermediates to make the salts.

10 Claims, No Drawings

PHOSPHATE-CARBOXYLATE COMPOUNDS

BACKGROUND OF THE INVENTION

This invention relates to phosphate-carboxylate compounds. Certain of the compounds are useful intermediates in the preparation of the alkali metal, ammonium or trialkanol ammonium salts of the compounds, which have utility as sequestrants, detergent builders, metal chelants, threshold agents and the like.

DESCRIPTION OF THE PRIOR ART

A wide variety of non-phosphorus polycarboxylate compounds have been developed and have been described in the prior art. For example, U.S. Pat. No. 3,704,320 describes ether polycarboxylates as useful chelants and sequestrants, but these and other compounds described in the prior art relate to non-phosphorus compounds of readily distinguishable molecular structure.

On the other hand, some phosphorus-containing polycarboxylates are known to the art. For example, U.S. Pat. No. 4,014,959 discloses phosphonoether polycarboxylates as useful sequestering agents and Friedkin and Lehninger, J. BIOL. CHEM., Vol. 169, page 183 (1947) describe the preparation of phosphomalates.

Despite the teachings in these and other references, the compounds of the present invention, which are readily distinguishable from the prior art compounds, provide surprisingly superior chelation and sequestration properties over the prior art compounds. The value of superior sequestrants in various industrial and domestic water treating and cleaning applications is well understood by those skilled in the art, and the provision of novel sequestering agents to permit selection of optimum formulations for particular applications is a continuing need.

SUMMARY OF THE INVENTION

These and other needs are provided by compounds having the formula:

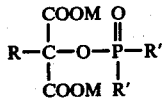

wherein R is selected from the group consisting of hydrogen and an alkyl group having from 1 to 4 carbon atoms, R' is selected from the group consisting of -OB and halogen, B is selected from the group consisting of alkali metal, ammonium, and trialkanolammonium having from 1 to 20 carbon atoms, and M is selected from the group consisting of B and alkyl having from 1 to 20 carbon atoms.

Broadly described, the compounds of the present invention can be prepared by bringing together in a reaction zone a phosphorus oxyhalide and a dialkyl alkyltartronate in the presence of a suitable solvent to produce a dialkyl alkyltartronyl phosphorodihalodate represented by the formula:

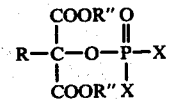

where R is selected from the group consisting of hydrogen and an alkyl group containing from 1 to 4 carbon atoms, X is a halogen, and R" is an alkyl group having from 1 to 20 carbon atoms. The alkyltartronyl phosphorodihalodate can then be hydrolyzed with a base by techniques known to those skilled in the art. The compound within the scope of the present invention after hydrolysis with a base, such as an alkali metal hydroxide, can be represented by the formula:

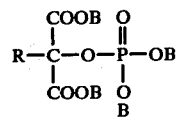

where B is an alkali metal and R is as defined above. The ammonium or trialkanol ammonium salts can be prepared by exchange of the alkali metal on the carboxylate with ammonium or trialkanol ammonium by well known ion exchange procedures.

Any of the phosphorus oxyhalides, i.e., phosphorus oxyfluoride, phosphorus oxychloride, phosphorus oxybromide and phosphorus oxyiodide, can be used to prepare the compounds of the present invention. However, because of its ready commercial availability and chemical reactivity, phosphorus oxychloride is preferred.

The dialkyl alkytartronates suitable to prepare the compounds of the present invention are also those known to the art. The tartronate ester can be unsubstituted or can be substituted with an alkyl group containing 1 to 4, or higher, carbon atoms, although no beneficial result is seen when the tartronate ester is substituted with an alkyl group containing more than 4 carbon atoms. Preferred tartronates include unsubstituted tartronates, methyl tartronate, ethyl tartronate, isopropyl tartronate, propyl tartronate, isobutyl tartronate and butyl tartronate, i.e., wherein R in formula I is hydrogen or an alkyl group containing from 1 to 4 carbon atoms. The ester grouping can be an alkyl, cycloalkyl, aryl or alkyl aryl containing up to 20 carbon atoms in the group. The ester groups can be alike or unlike. Alkyl ester groups containing between 1 and 20 carbon atoms are preferred, and alkyl ester groups containing between 1 and about 4 carbon atoms are especially preferred, such as dimethyl tartronate, dimethyl alkyltartronate, diethyl tartronate, diethyl alkyltartronate, methylethyl tartronate, methyl ethyl alkyltartronate, dipropyl tartronate, diisopropyl alkyltartronate, dibutyl alkyltartronate and the like.

Any number of solvents known to those skilled in the art can be used to prepare the compounds of the present invention. It is only necessary that the solvent is chemically inert to the product of the reaction and to the starting materials, i.e., the phosphorus oxyhalide and the dialkyl alkyltartronate, and has some mutual solubility for the starting materials. Suitable solvents include, but are not limited to: tertiary amines, such as triethyl amine, tripropyl amine, tributyl amine, pyridine, alkyl pyridine, and the like; ethers, such as diethyl ether, diisopropyl ether, methylpropyl ether, diisopropyl ether, methylpropyl ether, dipropyl ether, and the like; hydrocarbons, both aliphatic and aromatic, having about 5 or more carbon atoms, such as hexane, heptane, octane, nonane, hexene, heptene, octene, benzene, toluene, xylene, cyclopentane, cyclopentene, cyclohexene, cycloheptane, and the like. Mixtures of solvents can be used such as a mixture of an ether with a hydrocarbon, or a mixture of an ether with a tertiary amine, say diethyl ether and triethyl amine.

The molar ratio of dialkyl alkyltartronate to phosphorus oxyhalide has an effect on the yield of the compound of the present invention. As will occur to those skilled in the art, when the ratio of dialkyl alkyltartronate to phosphorus oxyhalide is less than 1, the yield of the resulting dialkyl alkyltartronate phosphorodichloridate will be proportionately lower. However, when the molar ratio is greater than 1, compounds of the following types can be formed, depending on the ratio:

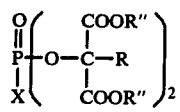

IV and when the molar ratio is above 2 and under more severe reaction conditions;

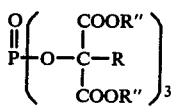

V or mixtures of the above with the compounds of the present invention. However, when these higher esters represented by formulas IV and V are subjected to basic hydrolysis, the higher esters tend to hydrolyze to form the monoester compounds of the present invention by splitting off the extra dialkyl alkyltartronate group from the phosphorus. Hence, it is preferred to use about an equimolar mixture of the phosphorus oxyhalide to the dialkyl alkyltartronate to prepare the compounds of the present invention.

The reaction between the dialkyl alkyltartronate and the phosphorus oxyhalide can be carried out at between subatmospheric pressures and superatmospheric pressures, and at temperatures between below 0° C. and above 100° C. The selection of pressure and temperature will depend on the particular starting materials for the reaction, the solvent used, and other factors well understood by those skilled in the art. However, when phosphorus oxychloride is reacted with diethyl methyltartronate using a mixture of diethyl ether and triethyl amine as the solvent, the reaction can be conducted at atmospheric pressure at temperatures between about 0° C. and 25° C.

The phosphate esters represented by formulas II, IV and V above are useful as intermediates to form the salts of alkyltartronyl phosphates of the present invention, which are themselves useful as chelants, sequesterants, threshold agents, anti-calculus agents, detergent builders and the like. It is only necessary to react the phosphorodihalodate with an aqueous base, such as an alkali metal hydroxide like lithium hydroxide, sodium hydroxide or potassium hydroxide, or such as an alkali metal carbonate like sodium carbonate, and the like, to form the tetraalkali metal salt of the alkyltartronyl phosphate. The conditions for such a hydrolysis are well known to those skilled in the art. However, an acid hydrolysis should be avoided since the esters are somewhat unstable, especially over several months time, if left in the acid form. The ammonium or alkanol ammonium salts can be prepared by well known ion exchange techniques using the alkali metal salts. As is known to those skilled in the art, the alkyl group on the alkanol ammonium can contain up to 20 carbon atoms, although lower alkyl containing from 1 to about 4 carbon atoms are preferred.

The salt forms of the compounds of the present invention are particularly useful as a builder in detergent formulations. The use of the alkali metal salts of the compounds, particularly the sodium salt, is preferred. However, in some formulations (such as liquid formulations where greater builder solubility is required) the use of ammonium or alkanol ammonium salts may be desirable.

The detergent formulations will contain at least 1 percent by weight and preferably at least 5 percent by weight of the salt forms of the compounds of this invention. In order to obtain the maximum advantage of the builder compositions of this invention the use of from 5 percent to 75 percent of these salts is preferred. The salt compounds of this invention can be the sole detergency builder or these compounds can be utilized in combination with other detergency builders which may constitute from 0 to 95 percent by weight of the total builders in the formulation. By way of example, builders which can be employed in combination with the novel salt compounds of this invention include water insoluble inorganic builders such as sodium aluminosilicates, sometimes known as zeolites, and water soluble inorganic builder salts, such as alkali metal polyphosphates, i.e., the tripolyphosphates and pyrophosphates, alkali metal carbonates, borates, bicarbonates and silicates, and water soluble organic builders, including aminopolycarboxylic acids and salts such as alkali metal nitrilotriacetates, cycloalkane polycarboxylic acids and salts, ether polycarboxylates, alkyl polycarboxylates, epoxy polycarboxylates, tetrahydrofuran polycarboxylates such as 2,3,4,5, or 2,2,5,5 tetrahydrofuran tetracarboxylates, benzene polycarboxylates, oxidized starches, amino (trimethylene phosphonic acid) and its salts, diphosphonic acids and salts (e.g., methylene diphosphonic acid; 1-hydroxy ethylidene diphosphonic acid) and the like.

The detergent formulations will generally contain from 5 percent to 95 percent by weight total builder (although greater or lesser quantities may be employed if desired) which, as indicated above, may be solely the builder salt compounds of this invention or mixtures of such compounds with other builders. The total amount of builder employed will be dependent on the intended use of the detergent formulation, other ingredients of the formulation, pH conditions and the like. For example, general laundry powder formulations will usually contain 20 percent to 60 percent builder; liquid dishwashing formulations 11 percent to 12 percent builder; machine dishwashing formulations 60 percent to 90 percent builder. Optimum levels of builder content as well as optimum mixtures of builders for various uses can be determined by routine tests in accordance with conventional detergent formulation practice.

The detergent formulations will generally contain a water soluble detergent surfactant although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, e.g., salts of fatty acids derived from coconut oil and tallow; alkyl benzene sulfonates—particularly linear alkyl benzene sulfonates in which the alkyl group contains from 10 to 16 carbon atoms; alcohol sulfates; ethoxylated alcohol sulfates; hydroxy alkyl sulfonates, alkenyl and alkyl sulfates and sulfonates; monoglyceride sulfates; acid condensates of fatty acid chlorides with hydroxy alkyl sulfonates and the like.

Examples of suitable nonionic surfactants include alkylene oxide (e.g., ethylene oxide) condensates of mono and polyhydroxy alcohols, alkyl phenols, fatty acid amines, and fatty amines; amine oxides, sugar derivatives such as sucrose monopalmitate; long chain tertiary phosphine oxides, dialkyl sulfoxides; fatty acid amides, (e.g., mono- or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecyl ammonio)propane-1-sulfonate and 3-(N,N-dimethyl-N-hexadecyl ammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well understood practices of detergent formulation. For example, anionic surfactants, particularly linear alkyl benzene sulfonate are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5 percent to 50 percent surfactant by weight, although as much as 95 percent or more surfactant may be employed if desired. For example, general laundry powder formulations normally contain 5 percent to 50 percent, preferably 15 percent to 25 percent surfactant; machine dishwashing formulations 0.5 percent to 5 percent; liquid dishwashing formulations 20 percent to 45 percent. The weight ratio of surfactant to builder will generally be in the range of from 1:12 to 2:1.

In addition to builder and surfactant components, detergent formulations may contain fillers such as sodium sulfate and minor amounts of bleaches, dyes, optical brighteners, soil anti-redeposition agents, perfumes and the like.

DESCRIPTION OF THE PREFERRED EMBODIMENTS

The invention is further illustrated by, but not limited to, the following examples wherein all parts and percentages are by weight unless otherwise indicated.

EXAMPLE I

This example illustrates the preparation of a prior art compound, tetrasodium phosphomalate.

A 500 ml. 4-necked, round bottom flask equipped with a magnetic stirrer, reflux condenser, gas scrubber and thermometer, was charged with 84 g. phosphorus oxychloride. To this was added 94.4 g. phenol. A very endothermic reaction occurred. The contents were slowly heated to 180° C., cooled to room temperature, and the residue vacuum distilled at 0.4 Torr. Two fractions were obtained. The first cut (25°–100° C.) consisted of 100 ml. material containing some phenol and mostly

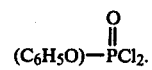

The second cut of 30 g. (100°–135° C.) was mostly

The first cut was treated with an additional 30 g. phenol, heated to 180° C. for 4 hours and redistilled at 110°–130° C. at 0.4 Torr to give an additional 30 g. of material. This was combined with the second cut noted above and was redistilled at 115° C.–125° C. at 0.4 Torr to give 50.4 g.

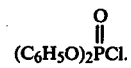

A 250 ml. 3-necked, round bottom flask equipped with a mechanical stirrer was charged with 34 g. pyridine and 50.4 g. of the

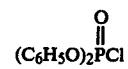

prepared above. A solution of 35.7 g. diethyl malate in 20 ml. pyridine was added dropwise with cooling. An exothermic reaction occurred and pyridine hydrochloride precipitated after 5 to 10 minutes. The reaction was left standing for two days.

The reaction mixture was poured into 300 ml. water and adjusted to pH 8 with 50% sodium hydroxide. The contents were transferred to a separatory funnel and extracted three times with 200 ml. portions of diethyl ether to give a yellow ethereal solution. The ether layer was dried over magnesium sulfate and the ether was removed on a rotary evaporator to give 70.7 g. (91 percent) yellow oily residue after pumping under vacuum overnight at room temperature. The compound was analyzed by proton magnetic resonance to confirm the presence of the ester.

Ten grams of the above ester in 300 ml. ethanol was mixed with 0.9 g. platinum oxide catalyst and hydrogenated at room temperature in a 1 liter suction flask with stirring. The hydrogenolysis was 50 percent complete after 1 day and complete after 2 days. The solution was filtered to remove the catalyst and the ethanol was removed on a rotary evaporator. The residue was pumped under vacuum for 3 hours to give 6.7 g. oily residue. The oily residue was slurried in 20 ml. water and 7.9 g. 50% sodium hydroxide was added to neutralize and saponify the acid-ester. The solution was stirred overnight at room temperaure. The water was removed at 40° C. under vacuum. The residue was treated with methanol and ground in a Waring blender to give 5.7 g. white solid after drying at 50° C. for 3 hours, in vacuo. The compound was confirmed by analysis in deuterium oxide using $P^{31}$ nuclear magnetic resonance. No orthophosphate due to hydrolysis was observed.

EXAMPLE II

This example illustrates the preparation of one of the preferred compounds of the invention, tetrasodium methyltartronyl phosphate.

A 500 ml. 4-necked, round bottom flask equipped with a mechanical stirrer, reflux condenser, thermometer and dropping funnel was charged with 200 ml. diethyl ether, 21 g. triethyl amine and 15.3 g. phosphorus oxychloride. The mixture was cooled in an ice bath and 19.0 g. diethyl methyltartronate in 25 ml. diethyl ether was added dropwise while cooling. The mixture was allowed to warm to room temperature and stand overnight. An additional 200 ml. diethyl ether was added. The mixture was transferred to a 1-liter separatory funnel and washed twice with 200 ml. portions of water, and once with 100 ml. saturated sodium chloride solution. The ether layer was dried over magnesium sulfate. After removal of the ether, 19.3 g. of a yellow oil remained.

The oil was distilled in a falling film molecular still at 80° C. under vacuum. The volatile fraction consisted of 15.5 g. of clear liquid. Proton magnetic resonance spectrum analysis and elemental analysis confirmed the preparation of diethyl methyltartronyl phosphorodichloridate.

A 250 ml. beaker equipped with a magnetic stirrer was charged with 14.0 g. of the phosphorodichloridate and 50 ml. water. Then, 14.6 g. 50% sodium hydroxide diluted to 50 ml. with water was slowly added. The solution was monitored with a pH meter and was not allowed to exceed pH 12. An additional 7.5 g. 50% sodium hydroxide was added and the solution was left overnight. The following morning the solution was adjusted to pH 10 with HCl. Water was removed on a rotary evaporator and the resulting solid was dried in vacuo at 50° C. for 2 hours to give 21.2 g. solids. Thermographic analysis showed 9.65 percent water and chloride analysis indicated 25.62 percent sodium chloride, leaving 64.73 percent tetrasodium methyltartronylphosphate.

EXAMPLE III

The tetrasodium phosphomalate and tetrasodium methyltartronyl phosphate from Examples I and II, respectively, were tested for detergency building capacity by the Divalent Electrode Test Procedure as described by E. A. Matzner et al in an article entitled "Organic Builder Salts as Replacements for Sodium Tripolyphosphate(I)", published in TENSIDE, Vol. 10, 1973, Nos. 3 and 5, pages 119–125 and 239–245.

The results of the Divalent Electrode Titration test are set forth in the following table:

TABLE I

| COMPOUND | A, mv | B, mv | C, ml | O, ml | A + B/R & D | % STP |
|---|---|---|---|---|---|---|
| Na$_4$ Phosphomalate | 39.0 | 30.8 | 6.9 | 7.7 | 4.79 | 65.6 |
| Na$_4$ Methyltartronyl phosphate | 50.5 | 37.2 | 6.4 | 7.1 | 6.50 | 89 |

The results indicate that the compounds of the present invention are superior to the prior art compounds and will serve as useful replacements for STP in detergent compositions and washing applications where low phosphorus-containing materials are desired. In the right-hand column of the above table the comparison of the efficiency of the compounds with sodium tripolyphosphate (STP) is indicated as a percent.

Additionally, tetrasodium methyltartronyl phosphate was tested for compatibility with chlorine bleach and exhibited a satisfactory compatibility.

EXAMPLE IV

Tetrasodium methyltartronyl phosphate and tetrasodium phosphomalate were also compared in standard detergency tests with STP both on cotton and on permanent press polyester cotton.

The results are shown in the following table:

TABLE 2

| | Detergency Performance of Builders | | | | | |
|---|---|---|---|---|---|---|
| | Cotton Detergency - ΔRd | | | PP-PE/C Detergency- ΔRd | | |
| Builder Sample | 50% Builder | 37.5% Builder | 25% Builder | 50% Builder | 37.5% Builder | 25% Builder |
| STP | 33.2 | 26.2 | 17.6 | 14.1 | 8.5 | 6.0 |
| Na$_4$ Phosphomalate | 22.6 | 18.9 | — | 8.0 | 7.8 | — |
| Na$_4$ Methyltartronyl phosphate | 28.5 | 21.0 | 18.8 | 14.8 | 11.3 | 6.8 |

In the above table ΔRd refers to the change in reflectance values obtained by measuring the brightness of fabrics tested before and after being washed by subjecting them to light and measuring the amount of reflected light by use of a standard reflectometer. This test is used as a conventional basis for evaluating the cleaning ability of detergent formulations. It will be seen that in the permanent press polyester/cotton detergency test tetrasodium methyltartronyl phosphate actually outperformed STP and came close to STP on the cotton detergency test. Tetrasodium methyltartronyl phosphate was 115% of STP on the permanent press polyester/cotton and 89% of STP on cotton.

EXAMPLE V

Tetrasodium methyltartronyl phosphate was also tested in the Particulate Soil Removal Test and was compared with STP.

The results are shown in the following table.

TABLE 3

| Particulate Soil Removal Performance Of Builders | |
|---|---|
| Builder Sample | Percent Soil Removed |
| No Builder | 31.4 |
| STP | 45.5 |
| Na$_4$ Methyltartronyl phosphate | 34.3 |
| Significant Difference = ± 2.5 at 95% confidence | |
| Test Formulation: | 18% alkyl benzene sulfonate, 12% Silicate, 1% carboxymethyl cellulose (65%), 30% Builder, 30% Sodium Sulfate, Water |
| Test Conditions: | 0.12% Detergent Concentration, 49° C., Zero PPM Hardness, Cotton |

TABLE 3-continued

Particulate Soil Removal Performance Of Builders

| Builder Sample | Percent Soil Removed |
|---|---|
| Fabric Soiled with Bandy Black Clay, 8.9 pH | |

Note that while tetrasodium methyltartronyl phosphate did not perform as well as STP, it was significantly better than the control, i.e., where no builder was used, confirming its performance in the removal of particulate soil in this standard test.

Although the invention has been described in terms of specified embodiments which are set forth in considerable detail, it should be understood that this is by way of illustration only, and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed is:

1. A compound having the formula:

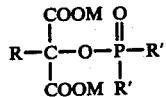

wherein

R is selected from the group consisting of hydrogen and an alkyl group having from 1 to 4 carbon atoms;

R' is selected from the group consisting of —OB and halogen; and

B is selected from the group consisting of alkali metal, ammonium and trialkanolammonium having from 1 to 20 carbon atoms, and M is selected from the group consisting of B and alkyl having from 1 to 20 carbon atoms.

2. A compound of claim 1 wherein R' is a halogen.
3. A compound of claim 2 wherein R' is chlorine.
4. A compound of claim 2 wherein M is an alkyl having from 1 to 20 carbon atoms.
5. A compound of claim 2 wherein M is an alkyl having from 1 to 4 carbon atoms.
6. A compound of claim 2 having the formula:

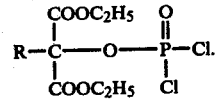

7. A compound of claim 6 wherein R is $CH_3$.
8. A compound of claim 1 having the formula:

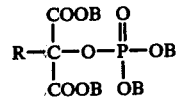

wherein B is an alkali metal.

9. A compound of claim 8 wherein R is methyl.
10. A compound of claim 8 wherein B is sodium.

* * * * *